(12) United States Patent
Gu et al.

(10) Patent No.: US 12,168,793 B2
(45) Date of Patent: Dec. 17, 2024

(54) METHOD OF ENZYMATICALLY PREPARING N-3 POLYUNSATURATED FATTY ACID DIACYLGLYCEROL

(71) Applicant: Jiangnan University, Wuxi (CN)

(72) Inventors: Jialing Gu, Wuxi (CN); Xiaosan Wang, Wuxi (CN); Houyue Li, Wuxi (CN); Zhimian Liu, Wuxi (CN); Weijia Bao, Wuxi (CN); Zixin Wang, Wuxi (CN); Yifan Wang, Wuxi (CN); Yijie Fu, Wuxi (CN); Yujie Su, Wuxi (CN)

(73) Assignee: Jiangnan University, Wuxi (CN)

(*) Notice: Subject to any disclaimer, the term of this patent is extended or adjusted under 35 U.S.C. 154(b) by 0 days.

(21) Appl. No.: 18/317,144

(22) Filed: May 15, 2023

(65) Prior Publication Data
US 2024/0287557 A1    Aug. 29, 2024

(30) Foreign Application Priority Data
Feb. 24, 2023  (CN) .......................... 202310164194.8

(51) Int. Cl.
  *C12P 7/6472* (2022.01)
  *C12N 9/20* (2006.01)
  *C12R 1/72* (2006.01)

(52) U.S. Cl.
  CPC .............. *C12P 7/6472* (2013.01); *C12N 9/20* (2013.01); *C12R 2001/72* (2021.05)

(58) Field of Classification Search
None
See application file for complete search history.

(56) References Cited

FOREIGN PATENT DOCUMENTS

| CN | 113684230 | * 11/2021 | ............ C12P 7/6454 |
| WO | WO-2022156273 A1 | * 7/2022 | ............ A23D 9/007 |

OTHER PUBLICATIONS

Juttulapa, M. et al., "Effect of high-pressure homogenization on stability of emulsions containing zein and pectin," Asian Journal of Pharmaceutical Sciences 12: 21-27. (Year: 2017).*
Lo, S. et al., "Diacylglycerol Oil—Properties, Processes, and Products: A Review." Food Bioprocess Technol 1:223-233. (Year: 2008 ).*
Lupi, F., "A rheological analysis of structured water-in-olive oil emulsions." Journal of Food Engineering 107: 296-303. (Year: 2011).*
Li, Y. and Xiang, D., "Stability of oil-in-water emulsions performed by ultrasound power or high-pressure homogenization." PLoS One 14(3): e0213189 (Year: 2019).*

* cited by examiner

*Primary Examiner* — Suzanne M Noakes
*Assistant Examiner* — Ciara A McKnight
(74) *Attorney, Agent, or Firm* — IDEA Intellectual Limited; Margaret A. Burke; Sam T. Yip

(57) ABSTRACT

A method for enzymatically preparing a n-3 polyunsaturated fatty acid diacylglycerol using oil rich in n-3 polyunsaturated fatty acid as raw material to prepare diacylglycerol oil with selective enzymatic hydrolysis. Before the enzymatic reaction, the raw materials are homogenized to improve the catalytic efficiency of lipase in the hydrolysis and achieve the purpose of reducing the reaction time and the addition amount of lipase. As a result, the cost of industrial diacylglycerol preparation is reduced, ultimately reducing the cost of industrial diacylglycerol preparation. Therefore, the present invention provides an effective, mild and low-cost enzymatic method for preparing diacylglycerol rich in n-3 polyunsaturated fatty acids, which has a promising potential for industrial application.

10 Claims, No Drawings

METHOD OF ENZYMATICALLY PREPARING N-3 POLYUNSATURATED FATTY ACID DIACYLGLYCEROL

CROSS-REFERENCE TO RELATED APPLICATIONS

The present application claims priority from the Chinese patent application No. 202310164194.8 filed on Feb. 24, 2023, and the disclosure of which is incorporated herein by reference in its entirety.

FIELD OF THE INVENTION

The present invention generally relates to the field of food biotechnologies. More specifically the present invention relates to a method for preparing n-3 polyunsaturated fatty acid diacylglycerol using enzyme.

BACKGROUND OF THE INVENTION

Diacylglycerol (DAG), also known as diglyceride, is a functional oil produced by hydrolyzing a fatty acid of a triglyceride, which includes 1,2-diacylglycerol and 1,3-diacylglycerol. Although diacylglycerol content is typically less than 5% in most oils and fats, the content of diacylglycerol, especially 1,3-diacylglycerol, is considered to be beneficial. Recent animal experiments have demonstrated that oils containing diacylglycerol are effective in weight control, reducing blood fat levels, and decreasing uric acid. Additionally, n-3 polyunsaturated fatty acids have anti-inflammatory, anti-cancer and many other benefits. Therefore, developing diacylglycerol oils that are rich in n-3 polyunsaturated fatty acids holds significant market potential.

Diacylglycerol oil is traditionally prepared through high-temperature partial hydrolysis, which is widely used and cost-effective as it uses water a medium without requiring catalysts. However, this method has a drawback as partial glycerol, such as monoglycerides and diacylglycerol), in hydrolyzed products can form harmful substances, such as glycidyl esters and chloropropanol esters, when subjected to high temperature treatment. As a result, diacylglycerol oils prepared through this method often have a high content of harmful substances. In recent years, the use of lipase in the preparation of diacylglycerol oil has gained popularity. Enzymatic esterification, enzymatic glycerolysis, and enzymatic hydrolysis are some of the main methods used. Enzymatic preparation of diacylglycerol has several advantages, including mild reaction conditions and low content of harmful substances. However, the high cost of lipase limits its application in the industrialization of diacylglycerol.

There is still an urgent need of an economic, efficient, and mild preparation method that enriches n-3 polyunsaturated fatty acid diacylglycerol in manufacture, reduces the amount and cost of lipase addition, improves the reaction efficiency of enzymatic hydrolysis, shortens the hydrolysis time, and enhances the application effect and prospects of lipase in the preparation of n-3 polyunsaturated fatty acid diacylglycerol.

SUMMARY OF THE INVENTION

The purpose of this section is to outline certain aspects of the embodiments of the present invention and to provide a brief introduction of some preferred embodiments. Some simplifications or omissions may be made in this section, as well as in the abstract and titles of the present invention, in order to avoid ambiguity of the purpose of this section, the abstract and titles, and such simplifications or omissions shall not be used to limit the scope of the present invention.

In view of the technical problems existing in the aforementioned and/or prior art, the present invention is proposed.

In accordance with a first aspect of the present invention, a method for enzymatically preparing a n-3 polyunsaturated fatty acid diacylglycerol is provided. Particularly, the method uses oils rich in n-3 polyunsaturated fatty acid as raw materials to prepare diacylglycerol by employing selective enzymatic hydrolysis method. Before the enzymatic reaction, the reaction raw materials are homogenized to improve the catalytic efficiency of lipase in the hydrolysis mixed reaction system.

To address the aforementioned technical problems, the present invention provides the following technical solutions: a method for enzymatically preparing n-3 polyunsaturated fatty acid diacylglycerols, including the following steps:
   adding an oil and water to a reactor for a high-pressure homogenization;
   adding a lipase for undergoing an enzymatic reaction;
   removing the water and the lipase after the reaction; and
   separating free fatty acids and obtaining a diacylglycerol oil.

In accordance with one embodiment of the present invention, the high-pressure homogenization is carried out at a homogenization pressure of at least 10 MPa for a homogenization time at least 1 minute.

In accordance with another embodiment of the present invention, the high-pressure homogenization is carried out at a homogenization pressure ranging from 35 to 75 MPa for a homogenization time of 3-12 minutes.

In accordance with one embodiment of the present invention, the lipase includes a lipase derived from *Candida cylindracea*.

In accordance with one embodiment of the present invention, the lipase has an addition amount less than 0.2 wt. % of the weight of the oil.

In accordance with another embodiment of the present invention, the water has an addition amount of 20%-50% of the weight of the oil.

In accordance with one embodiment of the present invention, the enzymatic reaction is conducted at a reaction temperature of 20-50° C. for a reaction time of 3-8 hours.

In accordance with one embodiment of the present invention, the method further includes adding an emulsifier to the reactor as one of the reaction substrates before the high-pressure homogenization.

In accordance with one embodiment of the present invention, the emulsifier includes an unsaturated fatty acid monoglyceride and/or a medium-chain fatty acid monoglyceride.

In accordance with one embodiment of the present invention, the emulsifier has an addition amount more than 0.2% of the weight of the oil.

In accordance with a second aspect of the present invention, the present invention provides applications of the enzymatic method for preparing n-3 polyunsaturated fatty acid diacylglycerol in the fields of food and medicine as described in any one of the above. For instance, a usage of a pharmaceutical composition including the diacylglycerol oil obtained from the above method for treating a disease or a condition, or a usage of a composition including the diacylglycerol oil of obtained from the above method for manufacturing a healthy food.

The present invention offers several advantages over prior art. The present invention homogenizes the reaction substrates (water and oil rich in n-3 polyunsaturated fatty acid)

to make them fully mixed before adding the lipase. This homogenization process significantly improves the hydrolysis efficiency of the substrates and shortens the reaction time. By allowing the reaction raw materials to undergo homogenous, the hydrolysis efficiency is increased, and the amount of lipase required is reduced. This leads to a reduction in the manufacturing cost of n-3 polyunsaturated fatty acid diacylglycerol, making it more cost-effective for enzymatic hydrolysis in the preparation of n-3 polyunsaturated fatty acid diacylglycerols oil.

DETAILED DESCRIPTION

To better illustrate and explain the objectives, characteristics and benefits of the present invention, specific implementation methods are described in detail below in conjunction with the embodiments of the specification.

In the following description, methods and applications of enzymatically preparing a n-3 polyunsaturated fatty acid diacylglycerol and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

The terms of "one embodiment" or "an embodiment" used herein refer to a specific feature, structure or characteristic that may be included in one or more implementations of the present invention. The term of "in one embodiment" appearing in various sections in this specification does not necessarily refer to the same embodiment, but may refer to a distinct or alternative embodiment that is not mutually exclusive with other embodiments.

Unless stated otherwise, the raw materials used in the embodiments are commercially available.

The diacylglycerol content is determined using HPLC according to the method and parameters described by Jiang Cong et al. in their publication "Concentration of n-3 polyunsaturated fatty acid glycerides by *Candida antarctica* lipase A-catalyzed selective methanolysis" (Food Bioscience, 2022, 46, 101562).

In accordance with a first aspect of the present invention, a method for enzymatically preparing a n-3 polyunsaturated fatty acid diacylglycerol is provided.

In one embodiment, the method including the following steps:
adding an oil and water to a reactor for a high-pressure homogenization;
adding a lipase for undergoing an enzymatic reaction;
removing the water and the lipase after the reaction; and
separating free fatty acids and obtaining a diacylglycerol oil.

In one embodiment, the oil is an oil rich in n-3 polyunsaturated fatty acid and the content of n-3 polyunsaturated fatty acid is 30% to 70%.

In one embodiment, the high-pressure homogenization is carried out at a homogenization pressure of at least 10 MPa for a homogenization time of at least 1 minute.

In one embodiment, the high-pressure homogenization is carried out at a homogenization pressure ranging from 35 to 75 MPa for a homogenization time of 3-12 minutes.

In one embodiment, the lipase includes a lipase derived from *Candida cylindracea*.

In one embodiment, the lipase has an addition amount less than 0.2 wt. % of the weight of the oil.

In one embodiment, the water has an addition amount of 20%-50% of the weight of the oil.

In one embodiment, the enzymatic reaction is conducted at a reaction temperature of 20-50° C. for a reaction time of 3-8 hours.

In one embodiment, the method further includes adding an emulsifier to the reactor before the high-pressure homogenization.

In one embodiment, the emulsifier includes an unsaturated fatty acid monoglyceride and a medium-chain fatty acid monoglyceride.

In one embodiment, the emulsifier has an addition amount more than 0.2% of the weight of the oil.

In one embodiment, the present invention provides applications of the enzymatic method for preparing n-3 polyunsaturated fatty acid diacylglycerol in the fields of food and medicine as described in any one of the above.

EXAMPLES

Example 1

To prepare the samples, 200 g of refined tuna oil (containing 36.3% of n-3 polyunsaturated fatty acid) and 100 g of water are mixed and subjected to homogenization at different homogenization pressures (15-45 MPa) for 8 minutes. Following the homogenization process, 0.2 g of Lipase AY 400 SD lipase (from *Candida cylindracea*) is added for enzymatic hydrolysis. The reaction is carried out at 36° C. for various durations (2 to 8 hours) before removing the water and lipase. The crude products are sampled and analyzed for the diacylglycerol content, and the results are summarized in Table 1.

TABLE 1

Effects of different homogenization pressure and hydrolysis time on the diacylglycerol content in crude product

| homogenization pressure | 15 MPa | | | | 25 MPa | | | | 35 MPa | | | | 45 MPa | | | |
| --- | --- | --- | --- | --- | --- | --- | --- | --- | --- | --- | --- | --- | --- | --- | --- | --- |
| hydrolysis time (h) | 2 | 4 | 6 | 8 | 2 | 4 | 6 | 8 | 2 | 4 | 6 | 8 | 2 | 4 | 6 | 8 |
| Diacylglycerol content (%) | 18.3 | 28.4 | 33.2 | 34.8 | 21.6 | 33.1 | 36.7 | 31.2 | 22.9 | 35.8 | 37.2 | 30.5 | 25.5 | 36.7 | 37.9 | 30.3 |

When the reaction substrates (tuna oil and water) are not homogenized before the enzymatic reaction, the diacylglycerol content in the product reached equilibrium after 8 hours of enzyme reaction catalyzed by 0.1% lipase, at which point the content of diacylglycerol is the highest at 31.3%. With continuously increasing the hydrolysis time, the content of diacylglycerol in the product gradually decreased, and the diacylglycerol content in the product drops to 27.5% when the reaction time is increased to 10 hours.

However, when the reaction substrates are homogenized under a pressure of 15 MPa before the enzymatic hydrolysis, the time required for the reaction to reach equilibrium is reduced from 8 hours to 6 hours compared with the above unhomogenized group. When the homogeneous pressure is increased to 45 MPa, the time required for the reaction to reach equilibrium is further shortened. As shown in Table 1, the homogeneous treatment of the substrate before the reaction significantly shortens the enzymatic hydrolysis time and increases the content of diacylglycerol in the crude product when the reaction reaches equilibrium.

As shown in Table 1, the reaction mixture homogenized under 45 MPa has reached equilibrium after reacting for 4 hours, and then increasing the reaction time leads to a decrease in the content of diacylglycerol in the crude product. Further, if the homogeneous pressure is increased to 60, 75 and 90 MPa and the hydrolysis time is set to 4 hours, the content of diacylglycerol in the crude product is 37.1%, 38% and 38.4%, respectively, showing that the diacylglycerol content in the crude product does not change much.

Based on the Quality Guidelines of The New Food Raw Material Protocol in China, diacylglycerol oil is stipulated that the content of monoglyceride and free fatty acid in it should be less than 1.5% and 0.5%, respectively, and the content of diacylglycerol should be higher than or equal to 40%. To ensure that the crude product meets these requirements after purification, molecular distillation is carried out as monoglyceride and diacylglycerol are difficult to separate while free fatty acid and diacylglycerol are easier to separate due to the differences in their properties. Although free fatty acids can easily meet the requirements after molecular distillation, meeting the requirements for monoglycerides is relatively challenging.

The hydrolyzed crude products obtained after 4 hours of enzymatic hydrolysis under different homogeneous pressures are used as raw material for molecular distillation under specific conditions, including a main evaporation temperature of 170° C., a condensation temperature of 30° C., and a vacuum degree of <0.001 mbar. After one round of distillation, the monoglyceride content and peroxide value of the crude product are measured and the results are presented in Table 2. It is observed that after distillation, the monoglyceride content meets the requirements of The New Food Raw Material Protocol.

TABLE 2

Effects of different homogeneous pressures on the monoglyceride and free fatty acid content, and peroxide value of the purified product

| Homogeneous pressure | 15 MPa | 25 MPa | 35 MPa | 45 MPa | 60 MPa | 75 MPa | 90 MPa |
|---|---|---|---|---|---|---|---|
| Monoglyceride content in purified product (%) | 0.39 | 0.58 | 0.70 | 0.74 | 0.88 | 1.02 | 1.34 |
| Free fatty acid content in purified product (%) | | | | <0.5 | | | |
| Peroxide value of purified product (mmol/kg) | 4.9 | 5.2 | 3.6 | 3.9 | 4.3 | 4.7 | 5.4 |

In accordance with the regulations for fish oil products, SC/T-3503-2000, the peroxide value of polyene fish oil products must not exceed 5.0 mmol/kg (≤5.0 mmol/kg). Therefore, it is preferable to use a homogenization pressure range of 35 MPa to 75 MPa.

Example 2

A mixture of 200 g of refined tuna oil (containing 36.3% of n-3 polyunsaturated fatty acid) and 60 g of water is homogenized at a homogenization pressure of 45 MPa for a while. After homogenization, 0.3 g of Lipase AY 30 SD lipase (from *Candida cylindracea*) is added for enzymatic hydrolysis. The reaction is performed at 36° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 3.

TABLE 3

Effects of homogenization duration on the diacylglycerol content in hydrolyzed crude product, and the monoglyceride content and the peroxide value of purified product

| Homogenization duration (min) | 0 | 3 | 6 | 8 | 12 | 15 | 18 | 22 |
|---|---|---|---|---|---|---|---|---|
| Diacylglycerol content in crude product (%) | 16.0 | 32.5 | 35.2 | 37.7 | 35.8 | 32.1 | 31.0 | 29.8 |
| Monoglyceride content in purified product (%) | | | | <1.5 | | | | |
| Peroxide value of purified product (mmol/kg) | | | <5.0 | | | | >5.0 | |

As shown in Table 3, the homogenization treatment can significantly enhance the catalytic efficiency of lipase and increase the diacylglycerol content in the hydrolyzed product under the same reaction time, compared to the non-homogenized group. After molecular distillation, its monoglyceride content still meets the requirements, but the peroxide value content is relatively high after a relatively long homogenization duration (≥15 min). Therefore, it is preferred that the homogenization time is around 6~12 min.

Example 3

A mixture of 200 g of refined tuna oil (containing 36.3% of n-3 polyunsaturated fatty acid) and 80 g of water is homogenized at a homogenization pressure of 35 MPa for 6 minutes. After homogenization, a certain amount of Lipase AY 400 SD lipase (from *Candida cylindracea*) is added for enzymatic hydrolysis. The reaction is performed at 36° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 4.

TABLE 4

Effects of enzyme addition amount and homogenization treatment time on the diacylglycerol content in crude product, and the monoglyceride content and the peroxide value in purified product

| Amount of lipase | 0.05 | | 0.10 | | 0.12 | | 0.15 | | 0.2 | |
|---|---|---|---|---|---|---|---|---|---|---|
| Homogenization duration (min) | 0 | 6 | 0 | 6 | 0 | 6 | 0 | 6 | 0 | 6 |

TABLE 4-continued

Effects of enzyme addition amount and homogenization treatment time on the diacylglycerol content in crude product, and the monoglyceride content and the peroxide value in purified product

| Diacylglycerol content in crude product (%) | 12.1 | 22.6 | 20.6 | 36.8 | 24.3 | 37.9 | 30.8 | 37.0 | 36.8 | 35.9 |
|---|---|---|---|---|---|---|---|---|---|---|
| Monoglyceride content in purified product (%) | | | | | <1.5 | | | | | |
| Peroxide value of purified product (mmol/kg) | | | | | <5.0 | | | | | |

As shown in Table 4, when the addition amount of lipase is below 0.15%, the homogeneous treatment of the reaction substrate is beneficial in improving the catalytic efficiency of lipase and increasing the content of diacylglycerol in products. However, when the addition amount of lipase is 0.2%, homogenization treatment has no significant effect on increasing the content of diacylglycerol in products under the same reaction conditions of 4 hours. It indicates that after homogenization treatment, the optimal hydrolysis time for high dose of enzyme addition is less than 4 hours, with the optimal time shortened to 3 hours. However, when the lipase addition is low (0.05%), the optimal hydrolysis time is more than 4 hours, with the best reaction time being 7 hours, regardless of whether homogenization is performed. When the reaction substrates are homogenized at 35 MPa for 6 minutes with the catalysis of 0.1% lipase, the content of diacylglycerol is the same as that of the control group without homogeneous treatment with the addition of 0.2% lipase. Therefore, it is suggested that diacylglycerol can be prepared using a low dose of enzyme, which is beneficial in greatly reducing the production cost of diacylglycerol.

Example 4

A mixture of 200 g of refined tuna oil (containing 36.3% of n-3 polyunsaturated fatty acid) and 80 g of water is homogenized at a homogenization pressure of 35 MPa for 6 minutes. After homogenization, 0.1% of different lipase, including Lipase AY 400SD lipase from *Candida cylindracea*, a 1,3 specific lipase from *Thermomyces lanuginosus* (Lipozyme® TL IM), a lipase from *Candida antarctica* (Novozym® 435), Lipase PS from *Burkaholderia cepacian*, and a 1,3 specific lipase from *Rhizomucor miehei* (Lipozyme® RM), is added for enzymatic hydrolysis. The reaction is performed at 36° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 5.

TABLE 5

Effects of lipase types on the diacylglycerol content in crude product, and the monoglyceride content and the peroxide value of purified

| | Lipase | | | | |
|---|---|---|---|---|---|
| | AY 400SD | Lipozyme® TL IM | Novozym® 435 | Lipase PS | Lipozyme® RM IM |
| Diacylglycerol content in crude product (%) | 36.8 | 23.6 | 8.1 | 6.4 | 5.0 |
| Monoglyceride content in purified product (%) | | | <1.5 | | |
| Peroxide value of purified product (mmol/kg) | | | <5.0 | | |

As shown in Table 5, this example investigates the catalytic activity of five lipases (purchased from commercial enzyme companies) in hydrolyzing tuna oil. The results indicate that all five lipases partially hydrolyze tuna oil to diacylglycerol, with Lipase AY 400SD lipase from *Candida cylindracea* exhibiting the most effective catalytic effect, while Novozym® 435, Lipase PS and Lipozyme® RM IM show poor catalytic effect.

When Lipase AY 400SD and Lipozyme® TL IM are used as catalysts, and the reaction substrate is not homogenized, the diacylglycerol content in the crude product is 20.6% and 13.5%, respectively. After homogenization, the catalytic efficiency of lipase is significantly improved that the content of diacylglycerol is increased in the crude product.

Example 5

A mixture of 200 g of refined oils from different sources (containing different content of n-3 polyunsaturated fatty acid) and 80 g of water is homogenized at a homogenization pressure of 35 MPa for 6 minutes. After homogenization, 0.1% of Lipase AY 400 SD lipase (from *Candida cylindracea*) is added for enzymatic hydrolysis. The reaction is performed at 42° C. for 4 hours. After removing the water and lipase, it is sampled for analysis of its diacylglycerol content. The crude product 10 is then subjected to molecular distillation and sampled for analyzing its monoglyceride content and peroxide value. The results are summarized in Table 6.

TABLE 6

Effects of different types of reaction substrate oil on the diglyceride content in crude product and the monoglyceride content and the peroxide value of purified product

| Oil type | Soybean oil | Peanut oil | Canola oil | Seal oil (19.8% of n-3 PUFA) | Algae oil (50.3% of n-3 PUFA) | DHA structured lipid (70% of n-3 PUFA) | DHA structured lipid (80% of n-3 PUFA) |
|---|---|---|---|---|---|---|---|
| Diacylglycerol content (%) | 8.3 | 9.5 | 9.0 | 21.8 | 45.6 | 33.9 | 25.8 |
| Monoglyceride content in purified product (%) | | | | <1.5 | | | |
| Peroxide value of purified product (mmol/kg) | | | <5.0 | | | >5.0 | |

As shown in Table 6, when the common oils that do not contain n-3 polyunsaturated fatty acids (n-3 PUFA) such as peanut oil, rapeseed oil and soybean oil are used as raw materials for enzymatic hydrolysis to prepare diacylglycerol, the diacylglycerol content in the product is less than 10%. However, as the content of n-3 PUFA in the raw material increases, the diacylglycerol content in the enzymatically hydrolyzed product also increases. It is important to note that the content of n-3 PUFA in raw material should not be too high because, at a certain point, the diacylglycerol content in the hydrolyzed product will decrease. In addition, when the n-3 PUFA content in raw materials is high, the peroxide value in the final product is also high. Although the peroxide value of products can be reduced by adding silica gel or through an activated carbon adsorption process.

Example 6

A mixture of 200 g of refined tuna oil (containing 36.3% of n-3 polyunsaturated fatty acid), 80 g of water and 0.5 g of different types of emulsifiers (based on the weight of tuna oil) is homogenized at a homogenization pressure of 35 MPa for 6 minutes. After homogenization, 0.1% of Lipase AY 400 SD lipase (from *Candida cylindracea*) is added for enzymatic hydrolysis. The reaction is performed at 30° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 7.

As shown in Table 7, addition of monoglyceride emulsifier improves the reaction efficiency and increase the diacylglycerol content in crude products, especially medium-chain fatty acid monoglycerides (monoglyceride laurate) and unsaturated fatty acid monoglycerides (monoglyceride oleate) have significant effects on increasing the diacylglycerol content in final products. However, the long-chain saturated monoglyceride emulsifier and the other two emulsifiers do not improve the catalytic efficiency.

Example 7

A mixture of 200 g of refined tuna oil (containing 36.3% of n-3 polyunsaturated fatty acid), 80 g of water and a certain amount of monoglyceride oleate (based on the weight of tuna oil) is homogenized at a homogenization pressure of 35 MPa for 6 minutes. After homogenization, 0.1% of Lipase AY 400 SD lipase (from *Candida cylindracea*) is added for enzymatic hydrolysis. The reaction is performed at 30° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 8.

TABLE 7

Effects of different types of emulsifiers on the diacylglycerol content in crude product, and the monoglyceride content and the peroxide value of purified product

| Emulsifier | Sorbitan monolaurate | Polysorbate-20 | Monoglyceride laurate | Monoglyceride oleate | Monoglyceride stearate | No emulsifier |
|---|---|---|---|---|---|---|
| Diacylglycerol content (%) | 38.5 | 38.2 | 40.5 | 41.9 | 35.7 | 36.0 |
| Monoglyceride content in purified product (%) | | | <1.5 | | | |
| Peroxide value of purified product (mmol/kg) | | | <5.0 | | | |

TABLE 8

Effects of addition amount of monoglyceride oleate on the diacylglycerol content in crude product, and the monoglyceride content and the peroxide value of purified product

| | Addition amount of monoglyceride oleate | | | | |
|---|---|---|---|---|---|
| | 0.1% | 0.3% | 0.5% | 1% | 2% |
| Diacylglycerol content (%) | 36.7 | 38.2 | 41.9 | 41.2 | 40.5 |
| Monoglyceride content in purified product (%) | | | <1.5 | | >1.5 |
| Peroxide value of purified product (mmol/kg) | | | <5.0 | | |

As shown in Table 8, with the increase in addition amount of monoglyceride oleate from 0.1% to 0.5%, the diacylglycerol content in crude product increases from 36.7% to 41.9%. However, when the addition amount of monoglyceride oleate is continuously increasing to 1%, the diacylglycerol content in crude product has no significant change. On the other hand, if the addition amount of monoglyceride oleate reaches to 2%, the monoglyceride content in purified product is increased.

Example 8

A mixture of 200 g of refined 1812 tuna oil (containing 37.1% of n-3 polyunsaturated fatty acid) and a certain amount of water is homogenized at a homogenization pressure of 35 MPa for 6 minutes. After homogenization, 0.1% of Lipase AY 400 SD lipase (from *Candida cylindracea*) is added for enzymatic hydrolysis. The reaction is performed at 30° C. for 4 hours. After removing the water and lipase, it is sampled for analysis of its diacylglycerol content. The crude product is then subjected to molecular distillation and sampled for analyzing its monoglyceride content and peroxide value. The results are summarized in Table 9.

TABLE 9

Effects of water addition on the diacylglycerol content in crude product, and the monoglyceride content and the peroxide value of purified product

| Water addition (ml) | 20 | 40 | 60 | 80 | 100 | 150 | 200 |
|---|---|---|---|---|---|---|---|
| Diacylglycerol content (%) | 30.2 | 35.0 | 37.9 | 37.6 | 34.0 | 29.7 | 26.3 |
| Monoglyceride content in purified product (%) | | | | <1.5 | | | |
| Peroxide value of purified product (mmol/kg) | | | | <5.0 | | | |

As shown in Table 9, with the increase in addition amount of water from 10% to 30%, the diacylglycerol content in crude product increases from 30.2% to 37.9%. However, when the water amount increases from 30% to 50%, the diacylglycerol content in crude product drops to 34%. If the water amount is kept increasing, the diacylglycerol content is significantly reduced.

The present invention aims to prepare employs the oil rich in n-3 polyunsaturated fatty acids as raw materials to prepare diacylglycerol oil by selective enzymatic hydrolysis, particularly, the raw materials are homogenized prior to undergoing the enzymatic reaction. By homogenizing the raw materials, the catalytic efficiency of lipase is improved, resulting in a reduced reaction time and decreased addition amount of lipase. As a result, the cost of industrial diacylglycerol preparation is reduced, ultimately reducing the cost of industrial diacylglycerol preparation. Therefore, the present invention provides an effective, mild and low-cost enzymatic method for preparing diacylglycerol rich in n-3 polyunsaturated fatty acids, which has a promising potential for industrial application.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. A method for enzymatically preparing a n-3 polyunsaturated fatty acid diacylglycerol, comprising:
    adding an oil rich in n-3 polyunsaturated fatty acid and the content of n-3 polyunsaturated fatty acid is 30% to 70% and water to a reactor for a high-pressure homogenization;
    adding a lipase for undergoing an enzymatic reaction;
    removing the water and the lipase after the reaction; and
    separating free fatty acids and obtaining a diacylglycerol oil;
    wherein the high-pressure homogenization is carried out at a homogenization pressure of at least 10 MPa for a homogenization time of at least 1 minute.

2. The method of claim 1, wherein the high-pressure homogenization is carried out at a homogenization pressure ranging from 35 to 75 MPa for a homogenization time of 3-12 minutes.

3. The method of claim 1, wherein the lipase comprises a lipase derived from *Candida cylindracea*.

4. The method of claim 3, wherein the lipase has an addition amount less than 0.2 wt. % of the weight of the oil.

5. The method of claim 1, wherein the water has an addition amount of 20%-50% of the weight of the oil.

6. The method of claim 5, the enzymatic reaction is conducted at a reaction temperature of 20-50° C. for a reaction time of 3-8 hours.

7. The method of claim 1, wherein the method further comprises adding an emulsifier to the reactor before the high-pressure homogenization.

8. The method of claim 7, wherein the emulsifier comprises an unsaturated fatty acid monoglyceride and a medium-chain fatty acid monoglyceride.

9. The method of claim 8, wherein the emulsifier has an addition amount more than 0.2% of the weight of the oil.

10. A method for enzymatically preparing a n-3 polyunsaturated fatty acid diacylglycerol, comprising:
    adding an oil rich in n-3 polyunsaturated fatty acid and the content of n-3 polyunsaturated fatty acid is 30% to 70% and water to a reactor for a high-pressure homogenization;
    adding a lipase for undergoing an enzymatic reaction;
    adding an emulsifier to the reactor comprising an unsaturated fatty acid monoglyceride and a medium-chain fatty acid monoglyceride;
    removing the water and the lipase after the reaction; and
    separating free fatty acids and obtaining a diacylglycerol oil;

wherein the high-pressure homogenization is carried out at a homogenization pressure ranging from 35 to 75 MPa for a homogenization time of 3-12 minutes.

* * * * *